United States Patent
Prstojevich et al.

(10) Patent No.: US 8,224,429 B2
(45) Date of Patent: Jul. 17, 2012

(54) ADAPTIVE WATCH

(75) Inventors: Michael D. Prstojevich, Portland, OR (US); Christopher A. Robinette, Lake Oswego, OR (US); Theodore H. Helprin, Portland, OR (US); Charles W. Case, Jr., Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 133 days.

(21) Appl. No.: 12/498,197

(22) Filed: Jul. 6, 2009

(65) Prior Publication Data

US 2009/0270744 A1 Oct. 29, 2009

Related U.S. Application Data

(62) Division of application No. 11/690,766, filed on Mar. 23, 2007, now abandoned, which is a division of application No. 10/417,796, filed on Apr. 17, 2003, now abandoned.

(51) Int. Cl.
*A61B 5/04* (2006.01)

(52) U.S. Cl. .......................... 600/509; 600/519; 600/520

(58) Field of Classification Search ................. 600/509, 600/519; 482/1–9, 900–902
See application file for complete search history.

(56) References Cited

U.S. PATENT DOCUMENTS

| | | | |
|---|---|---|---|
| 4,566,461 A * | 1/1986 | Lubell et al. ................. 600/481 |
| 4,887,249 A | 12/1989 | Thinesen | |
| 5,769,755 A * | 6/1998 | Henry et al. ...................... 482/8 |
| 5,832,067 A | 11/1998 | Herold | |
| 5,886,952 A | 3/1999 | White | |
| 6,151,278 A | 11/2000 | Najarian | |
| 6,163,718 A * | 12/2000 | Fabrizio ......................... 600/519 |
| 6,587,127 B1 | 7/2003 | Leeke et al. | |
| 6,619,835 B2 | 9/2003 | Kita | |
| 6,753,882 B2 | 6/2004 | Nakazawa et al. | |
| 6,755,377 B1 | 6/2004 | Levin et al. | |
| 7,080,938 B1 | 7/2006 | Moore et al. | |
| 7,333,396 B1 | 2/2008 | Treyz et al. | |
| 2001/0004397 A1 | 6/2001 | Kita et al. | |
| 2002/0142887 A1* | 10/2002 | O' Malley .......................... 482/8 |
| 2003/0103413 A1 | 6/2003 | Jacobi | |
| 2003/0231551 A1 | 12/2003 | Saylor et al. | |
| 2004/0022130 A1 | 2/2004 | Chung | |
| 2004/0151071 A1 | 8/2004 | Kocher | |
| 2006/0075151 A1 | 4/2006 | Lin | |

* cited by examiner

*Primary Examiner* — Carl H Layno
*Assistant Examiner* — Paula J Stice
(74) *Attorney, Agent, or Firm* — Banner & Witcoff Ltd.

(57) ABSTRACT

A watch or other type of portable electronic console that employs a number of different functions in order to improve its usability. The watch may, for example, allow a user to connect the watch to one or more remote electronic devices, such as an electronic performance sensor or MP3 player. The watch then displays information related to the connected electronic devices. Still further, the watch may allow a user to control the operation of one or more connected remote electronic devices. Thus, if the watch is connected to a remote speed/distance monitor employing a calibration variable, then the watch may allow the user to adjust the calibration variable.

28 Claims, 7 Drawing Sheets

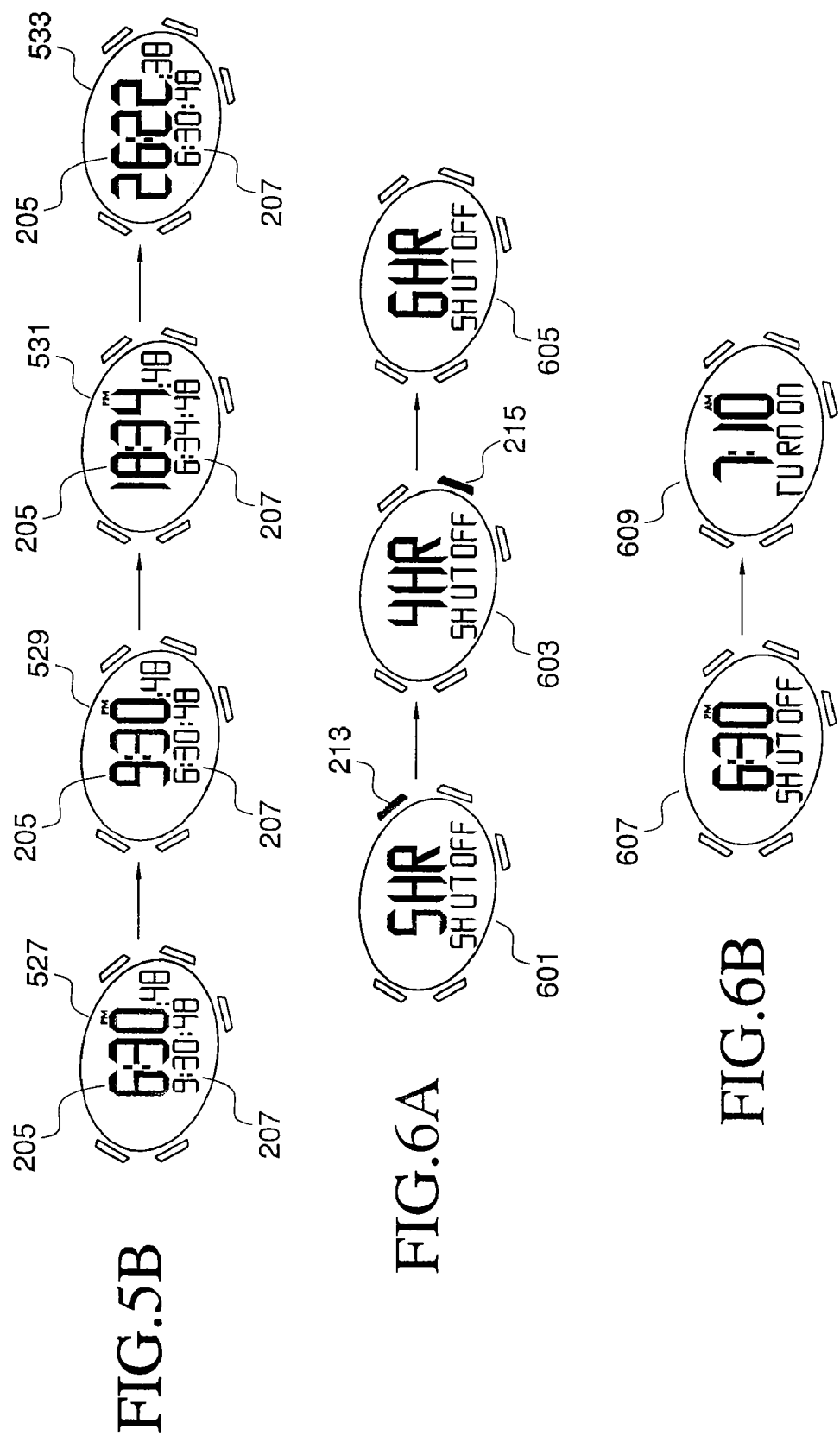

ADAPTIVE WATCH

CROSS-REFERENCE TO RELATED APPLICATION

This Non-Provisional U.S. patent application is a divisional application of and claims priority to U.S. patent application Ser. No. 11/690,766, which was filed in the U.S. Patent and Trademark Office on Mar. 23, 2007 and is entitled "Adaptive Watch now abandoned," which is a divisional application of U.S. patent application Ser. No. 10/417,796, which was filed in the U.S. Patent and Trademark Office on Apr. 17, 2003 and is entitled "Adaptive Watch." Each of these patent applications is entirely incorporated herein by reference.

FIELD OF THE INVENTION

Various aspects of the invention relate to an adaptive watch for athletic use. More particularly, various aspects of the invention relate to a watch or other portable electronic console that allows a user to connect the watch to one or more sensors or other remote electronic devices, such as a heart rate monitor, a speed/distance monitor, a blood pressure monitor, a global positioning device or even a digital music player, such that the watch displays information relating to the connected electronic devices. With particular regard to use with a speed/distance monitor, some aspects of the invention relate to a watch that allows a user to manually change a calibration variable for the speed/distance monitor. Still further, some aspects of the invention relate to a watch that allows the user to configure the display of the information provided by the watch, while still other aspects of the invention relate to a watch that enters into a power save mode when not in use. Various aspects of the invention also relate to a watch that automatically calculates various heart rate zones for a user. Additionally, some aspects of the invention relate to a watch that provides a plurality of different operational modes, with each operational mode including two or more different sub-modes of operation.

BACKGROUND OF THE INVENTION

In order to analyze their performance in a quantifiable manner, athletes will often measure various performance indicators. One class of performance indicators includes time parameters corresponding to an athlete's travel over a distance. For example, a runner may measure the total elapsed time required to run a distance, the elapsed time required to run a segment of a distance, and/or the average time required to run equal segments of a distance. Another class of performance indicator relates to the athlete's own physical parameters. Thus, an athlete may measure his or her heart rate, body temperature, blood pressure, or volumetric expansion of his or her lungs while performing an activity like running or biking.

To address the needs of such athletes, some watchmakers manufacture watches that work with a remote sensor device to measure one or more of these performance indicators. For example, some watchmakers manufacture watches that work with a distance monitor. The distance monitor may employ, for example, an accelerometer for measuring each step taken by an athlete. From this information, the monitor (or the associated watch) calculates the distance traveled by a user during a measured time. The watch then displays the measured distance and time. Some watchmakers also manufacturer watches that work with a heart rate monitor. The monitor rests on the user's chest, and electronically detects each of the user's heartbeats. The watch then displays the heart rate measured by the heart rate monitor.

Currently, however, these watches are configured to work with only specific sensors. Thus, if a user with a watch employing a speed/distance monitor also wishes to monitor his or her heart rate or monitor his or her blood pressure, the user cannot add a heart rate monitor or blood pressure monitor for use with his or her watch. Instead, the athlete must separately purchase and use a different watch with a heart rate monitor or blood pressure monitor. If the athlete then desires to measure a third performance indicator, the athlete must separately purchase and use yet another watch with the appropriate sensor. Accordingly, an athlete who wishes to measure multiple performance indicators must purchase and wear a corresponding number of watches, which is impractical and uncomfortable.

Also, as watches that measure athletic performance become more sophisticated, the amount of information gathered and displayed by these watches increases. The use of these watches has correspondingly grown more complex and difficult for a user to master. In particular, it may be difficult for a user to conveniently distinguish specific performance data that the user wishes to monitor from other performance data provided by the watch.

For example, a conventional watch for athletic use may have a variety of different operational modes for conveying different types of information. A watch may have a time or chronometer mode for displaying the current time in both the user's time zone and in another time zone. The same watch may also have a chronographic mode for measuring both a total elapsed time and individual lap times (that is, segments of a total elapsed time), and an alarm mode for activating and scheduling an alarm. It may also have a data mode for storing measured athletic information, such as previously recorded lap times. Still further, if the watch operates in conjunction with a sensor, such as a speed/distance monitor, then the watch may also have yet another mode of operation relating to the sensor.

The various operational modes of a conventional athletic watch can only be accessed by scrolling through each operational mode in sequence. Thus, in order for a user to switch from one operational mode to another operational mode, the user may have to scroll through several modes that the user does not wish to employ. Also, conventional athletic watches will display information in a fixed manner. Thus, an athletic watch may always show elapsed time information in a large font on a primary display, and only show heart rate information in a smaller font on a secondary display that is more difficult to read. On some occasions, however, an athlete may be more interested in his or her heart rate than in a total elapsed time. On these occasions, the athlete might prefer to have the heart rate information displayed in the larger font of the primary display, and have the elapsed time information displayed in the smaller font of the secondary display. Further, because of the number of additional functions now being incorporated into athletic watches, effectively controlling the consumption of power in these watches is more important than ever before.

Accordingly, there is a need for a watch or other portable electronic console that will allow the user to employ a variety of different electronic sensors for measuring athletic performance indicators. Still further, there is a need for a watch that can be more conveniently and easily used by athletes. In addition, there is a need for watch that efficiently conserves power when not in use.

SUMMARY OF THE INVENTION

Various examples of the invention may advantageously provide a watch or other type of portable electronic console that allows a user to connect the watch or portable electronic console to a plurality of other remote electronic devices, such as athletic performance monitors. For example, some embodiments of the invention may allow a user to connect a watch to any desired combination of athletic performance sensors, including one or more of a remote heart rate monitor, a speed/distance monitor, a blood pressure monitor, a bike pedometer, a volumetric expansion monitor, or a global positioning device. Alternately, or additionally, some embodiments of the invention may allow a user to connect a watch to other types of remote electronic devices, such as a music player that plays compact discs, mini discs, or a digital audio player for playing back compressed digital audio files, such as MP3 files or Microsoft Windows Media files.

Once a remote electronic device has been connected to the watch or other type of portable electronic console, then the watch or other type of console displays the information relevant to the electronic device. For example, if the watch is connected to a digital audio player then the watch will display the status information related to that digital audio player, such as the compressed digital audio file that it is currently playing, a listing of stored compressed digital audio files, the volume at which a file is to be played, and the like. The watch may also allow a user to control the operation of the digital audio player by manipulating control buttons on the watch. Alternately, if a watch is connected to an athletic performance sensor, such as a speed/distance monitor, then the watch will display the information gathered by the sensor. Again, the watch may additionally allow the user to control the operation of the connected sensor. For example, if the connected remote sensor is a speed/distance monitor employing a calibration variable, then the watch may allow a user to adjust the calibration variable for the speed/distance monitor through the watch.

Still further, an athletic watch or other portable electronic console according to various embodiments of the invention allows a user to configure the display of the information it provides. It may also employ a multi-tier menu, by which a user can more conveniently view information provided by the watch and control the operation of the watch. More particularly, the watch may employ two or more operational modes in a first tier, with each operational mode in the first tier then having one or more operational submodes in a second tier. Thus, if a user desires to employ two different submodes of operation within a single operational mode, the user need not scroll through any operational modes or submodes other than those within that single first-tier mode of operation. Still further, a watch according to various embodiments of the invention may enter into a power save mode when not in use, or when desired by the user. Still further, an athletic watch or other type of electronic portable console according to various embodiments of the invention may automatically calculate various data values to be used by an athlete, such as heart rate zones.

These and other features and aspects of the invention will be apparent upon consideration of the following detailed description of the different embodiments of the invention.

BRIEF DESCRIPTION OF THE DRAWINGS

FIGS. 5A and 5B illustrate various interface views that may be selected for display by the user interface shown in FIG. 2 according to various embodiments of the invention.

FIGS. 6A and 6B illustrates interface views that may be employed by various embodiments of the invention to implement a power saving function.

DETAILED DESCRIPTION

Overview

Various aspects of the invention relate to a watch or other type of portable electronic console that employs a number of different functions in order to improve its usability. For example, a watch according to some embodiments of the invention allows a user to connect the watch to one or more desired remote electronic devices, such as an electronic performance sensor or a digital audio player. The watch then displays information related to the connected electronic devices. Still further, the watch may allow a user to control the operation of one or more connected remote electronic devices. Thus, if the watch is connected to a digital audio player, then the watch may allow the user to view a menu of stored compressed digital audio files, select a particular digital audio file for playing, determine a volume for playing a file, and then play and subsequently stop the file. Similarly, if the watch is connected to a remote speed/distance monitor employing a calibration variable, then the watch may allow the user to adjust the calibration variable.

A watch or other type of portable electronic console according to various embodiments of the invention may also provide a multi-tiered menu for accessing its various functions. For example, each operational mode in the first tier may relate to a broad category of different functions of the watch, and may contain one or more operational submodes in a second tier. The submodes in the second tier may be used to perform specific functions related to the generic category of functions identified by the first-tier operational mode. Still further, a watch or other type of portable electronic console according to some embodiments of the invention may allow a user to conveniently select how the information provided by the watch is displayed. Further, a watch or other type of portable electronic console according to some embodiments of the invention may automatically calculate or select various data values for a user, such as heart rate zones for a user. Moreover, a watch or other type of portable electronic console according to some embodiments of invention includes a power save function that reduces the power consumption of the watch when it is not in use. Each of these features of a watch according to various embodiments of the invention will be discussed in detail below.

Exemplary Portable Console Device

Figure 1:
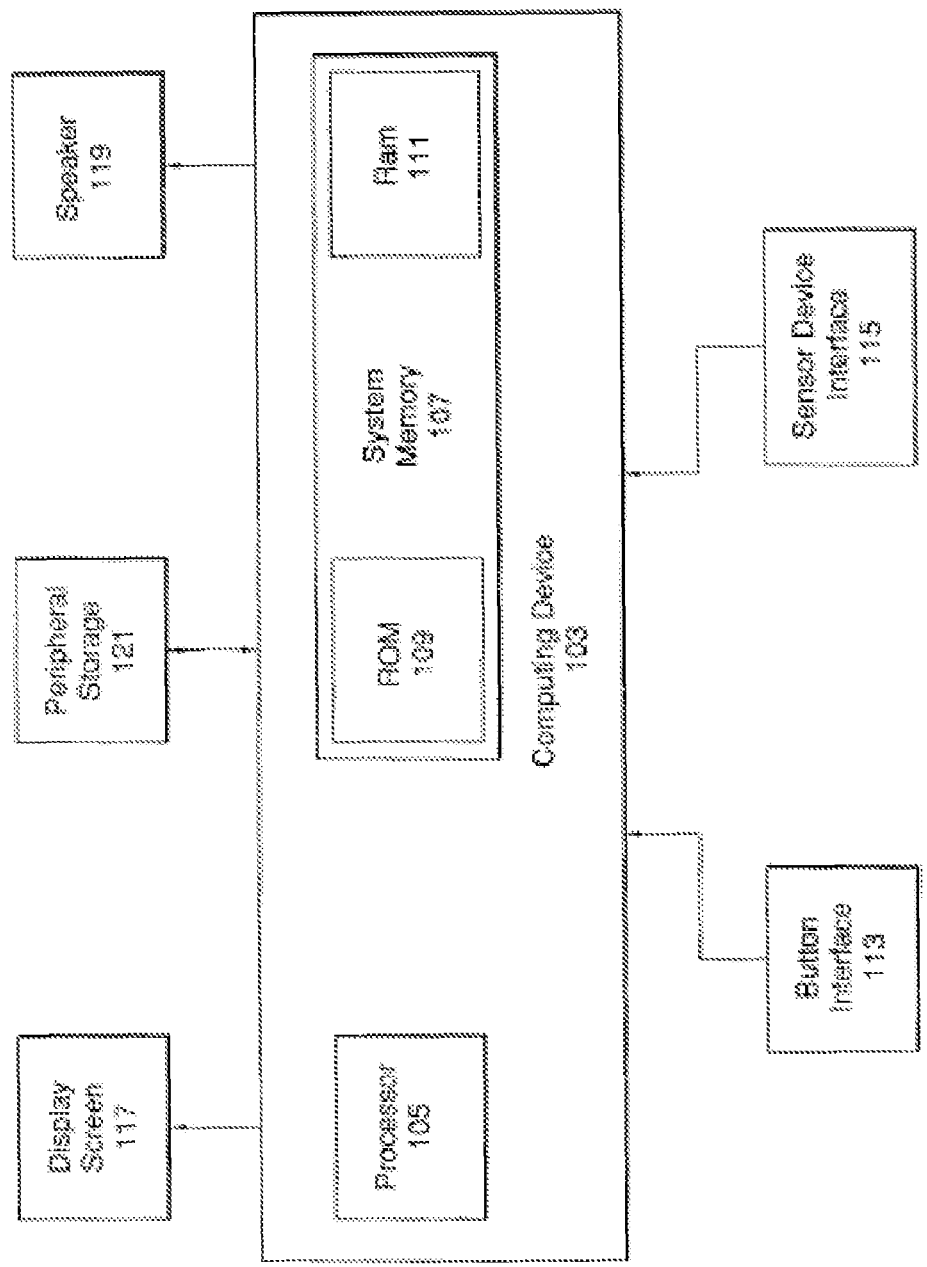
FIG. 1 is a block diagram of components of an electronic console according to an embodiment of the invention.

Various embodiments of the invention may conveniently be a portable electronic console implemented on a computer system. For example, some embodiments of the invention may be implemented by a portable computer system programmed to perform watch functions, such as a chronographic function, a chronometer function, and an alarm function. Accordingly, FIG. 1 illustrates an exemplary generalpurpose computer system that can be used to implement various aspects of the invention. In this figure, the computer system 101 has a computing device 103 that includes a processor 105, such as a programmable microprocessor, and a system memory 107 coupled to the processor 105. The system memory 107 may employ any appropriate memory device, such as a microcircuit memory device. The system memory 107 will typically include both a read only memory (ROM) 109 and a random access memory (RAM) 111. The ROM 109 and RAM 111 may be connected to the processor 105 using a suitable conventional bus structure (not shown), including a memory bus or memory controller, a peripheral bus, and a local bus using any of a variety of bus architectures.

The computer system 101 will also include one or more input devices. For example, the computer system may include a plurality of buttons for controlling the operation of the computer system 101. More particularly, the computer system 101 may include a button interface 113 having a small number of depressable buttons. It may also have one or more sensor interfaces 115 for providing information to and/or receiving information from sensor devices that measure one or more characteristics of the device's environment. For example, the sensor interfaces 115 may include a wireless transmitter and receiver for both sending and receiving information to and from remote sensors. For example, one or more sensor interfaces 115 may be capable of transmitting and receiving infrared signals, visible light signals, and signals encoded onto radio waves. Alternately, one or more sensor interfaces 115 may be physically connected to a remote sensor by a conductive wire or an optical fiber.

The computer system 101 will typically also include one or more output devices. For example, the computer system 101 may include a display 117, which may be a small liquid crystal display (LCD) screen, and one or more small speakers 119. Of course, the computer system 101 may have additional or alternate input, output, and memory devices as desired. For example, the computer system 101 may include a small peripheral data storage device 121, such as a Memory Stick or a Secure Digital card. As will be appreciated by those of ordinary skill in the art, the computer system 101 executes instructions stored in the system memory 107. These instructions may be stored and the system memory 107 when the computer system 101 is manufactured or the instructions may be retrieved to the system memory 107 from one or more peripheral storage devices. In addition, the computer system 101 may receive input data for executing the instructions from a user through one or more of the input devices. The computer system 101 may then output the results obtained by executing the instructions through one or more of the output devices.

Figure 2:
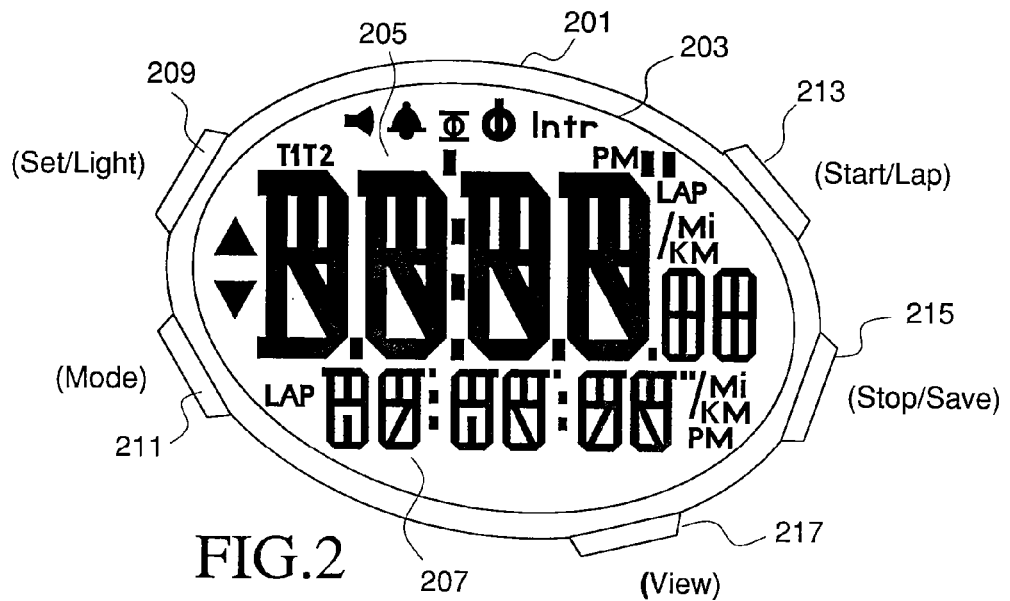
FIG. 2 illustrates a user interface provided by a watch according to an embodiment of the invention.

FIG. 2 illustrates one embodiment of a watch 201 implemented using the computer system 101 described above. As seen in this figure, the watch 201 includes a display 203, which displays data values calculated by, or provided to, the watch 201. More particularly, the display 203 includes a primary display field 205 and a secondary display field 207. The display 203 also includes a variety of icon displays for indicating operation processes of the watch 201. As also seen in this figure, the watch 201 includes five input command buttons 209-217. As will be explained in detail below, activating the first input command button 209, referred to as the "set/light" command button, allows a user to set values that will be used by the watch 201. The second input command button 211, referred to as the "mode" command button, allows a user to switch between various operational modes of the watch 201. The third input command button 213, referred to as the "start" command button, can be used to, for example, start various functions of the watch 201, such as a chronographic process.

The fourth input command button 215, referred to as the "stop" command button, can be used to, for example, stop various functions of the watch 201, such as the chronographic process. Lastly, the fifth command button 217, referred to as the "view" command button, allows a user to select the information displayed by the watch 201, and to switch between operational submodes of the watch. As will be discussed in detail below, one or more of these command buttons 209-217 may also perform alternate functions for various embodiments of the invention. Of course, other embodiments of the invention may employ more or fewer command buttons, or may employ alternate input devices altogether for receiving commands from a user.

Adaptive Watch

As discussed above, various embodiments of the invention relate to a watch or other type of portable electronic console that may work with two or more different remote electronic devices, such as sensors for measuring the parameters of an athlete's performance. That is, various embodiments of the invention relate to a watch or other portable electronic console that can be "adapted" to work with different electronic devices. As will be explained in detail below, with some embodiments of the invention the electronic portable console according to the invention simply receives and displays information provided by the remote electronic devices. With other embodiments of the invention, however, the electronic portable console will both receive and transmit information to remote electronic devices.

Figure 3A:
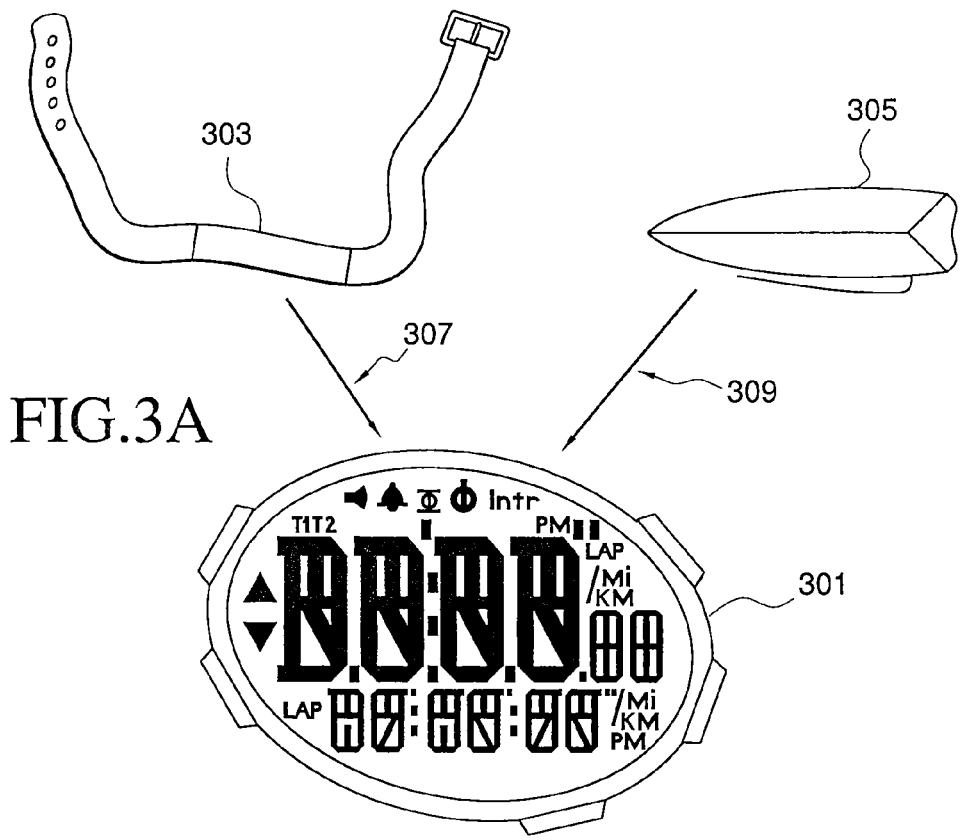
FIGS. 3A and 3B illustrate interactions of a watch with multiple sensors according to two embodiments of the invention, respectively.

More particularly, according to one embodiment of the invention shown in FIG. 3A, a portable electronic console 301 (the watch 201 in the illustrated example) receives measured sensor data from two separate remote electronic sensors 303 and 305, respectively. In this embodiment, the first electronic sensor 303 is a heart rate monitor, which monitors the rate at which a wearer's heart beats. The second remote electronic sensor 305 is a speed/distance monitor that measures a total distance traveled by the wearer. It should be appreciated, however, that additional or alternate sensors may be employed with the watch 301.

In this embodiment, both the heart rate monitor 303 and the speed/distance monitor 305 communicate with sensor device interfaces 115 of the watch 301 using a one-way wireless communication link 307 and 309, respectively. Both the heart rate monitor 303 and the speed/distance monitor 305 wirelessly transmit data messages to the sensor device interfaces 115 of the watch 301 at a rate of approximately one message per second, as will be explained in more detail below. The sensors 301 and 303 may encode the data message at a suitable rate, such as 2400 baud.

As will be appreciated by those of ordinary skill in the art, the baud rate and the message rate together determine the possible number of different messages that the watch 301 may receive. Thus, in the illustrated embodiment, the watch 301 may theoretically receive up to 48 different data messages per second (that is, the watch 301 may receive a data message from up to 48 different electronic devices per second). As will also be appreciated by those of ordinary skill in the art, however, the watch 301 will typically not be employed to communicate with the maximum number of possible electronic devices, to ensure that the data messages from different electronic devices do not conflict with or overlap each other. Instead, the watch 301 may typically receive data messages from approximately half its theoretical maximum number of electronic devices (that is, from approximately 24 different electronic devices per second).

The data messages from the sensors 303 and 305 may contain two different types of data. These are measured data and identification data. For example, with the heart rate monitor 303, the measured data will be the heart rate measured by the heart rate monitor 303 during its standard time unit. With the speed/distance monitor 305, the measure data may be combined distance and velocity information measured by the speed/distance monitor 305. For both the heart rate monitor 303 and the speed/distance monitor 305, the identification data will be data that uniquely identifies that sensor. For example, the identification data may include portions of a manufacturer's model number and/or serial number for that sensor.

In the illustrated embodiment, both the measured data and the identification data are encoded into a data word 16 bits long. Measured data may be distinguished from identification data, however, by setting the first two bits of the data word high, to indicate that it contains identification data rather than measured data. The remaining 14 bits can then be used to transmit the identification data. The measured data is then encoded in the binary-coded decimal (BCD) format, which ensures that the two most significant bits of the measured data will never both be high at the same time. Of course, those of ordinary skill in the art will appreciate that, with alternate embodiments of the invention, the measured data and identification data can be encoded using more or fewer than 16 bits. As will also be appreciated by those of ordinary skill in the art, the measured data and identification data can be imbedded in a larger data message. For example, with the illustrated embodiment, both the heart rate monitor 303 and the speed/distance monitor 305 transmit data to the watch 301 with a data message 5 bytes long. This data message includes the 2-byte measured data or identification data, a 1-byte cyclic redundancy check (CRC) value, and a 1-byte preamble.

For the watch 301 to properly distinguish data messages sent by the heart rate monitor 303 and the speed/distance monitor 305 from data messages sent by other electronic devices, the watch 301 may initially engage in an individual identification process for each of the sensors 303 and 305. During this process, the user places both the watch 301 and the sensor 303 or 305 in an identification training state. While in this training state, the sensors 303 and 305 will transmit data messages containing identification data rather than measured data. That is, the sensor 303 or 305 will transmit data messages that uniquely identify the sensor.

On the other hand, in the training state, the watch 301 looks for data messages received by the sensor device interface 115 that contain identification information corresponding to a valid electronic device. More particularly, the sensor device interface 115 receives the data messages from the sensor 303 or 305. The computing device 103 then processes (e.g., decodes) the data messages, to recognize if any of the data messages contain identification information corresponding to a valid electronic device. A list of valid electronic devices with which the watch 301 will function may be listed in, for example, a lookup table stored in the system memory 107.

Upon entering the training state, the watch 301 will have stored a listing of electronic devices from which it already has identification data in the system memory 107. If, during the training state, the computing device 103 recognizes a received data message with identification data for a type of electronic device for which the watch 301 has not already received identification data, then the computing device 103 will store that received identification information in the system memory 107 as well. Thus, if the watch 301 has not already received information data from a heart rate monitor or a time distance monitor, it will recognize a data message containing identification data from both the heart rate monitor 303 and the speed/distance monitor 305 during its training state.

After leaving the training state, data messages with measured data transmitted by the sensor 303 or 305 are encoded using that sensor's identification data. For example, the CRC byte may be computed using both the measured data and the sensor's identification data. Thus, the computing device 103 can distinguish and ignore data messages received by the sensor device interface 115 from electronic devices for which the watch 301 does not have stored identification information. That is, after the user simultaneously engages the training state for the sensor 303 or 305 and the watch 301, the computing device 103 will only recognize data messages that can be properly decoded using the identification data for that sensor. This allows a user to employ the watch 301 and sensors 303 and 305 near another watch and sensor combination, without having the measured information contained in the data messages from the other sensors being recognized and displayed by the watch 301.

It should be noted that, with various embodiments of the invention, the watch 301 may employ additional techniques to distinguish data messages sent by one sensor from data messages sent by another sensor. For example, in the illustrated embodiment, the heart rate monitor 303 transmits a data message once every 1.03 ms, while the speed/distance monitor 305 transmits a data message once every 1.0 ms. Accordingly, even if data messages from both sensors 303 and 305 occasionally overlap, they typically will do so only infrequently. Further, when each sensor 303 and 305 enters a training state, it delays the next data message transmission by 7/20 of a second, changing the phase of the transmission. Thus, if the data messages from two sensors are overlapping too much to be distinguished by the watch 301, a user can simply cause one of the sensors 303 or 305 to reenter the training state to shift the phase if its data message transmissions.

Figure 3B:
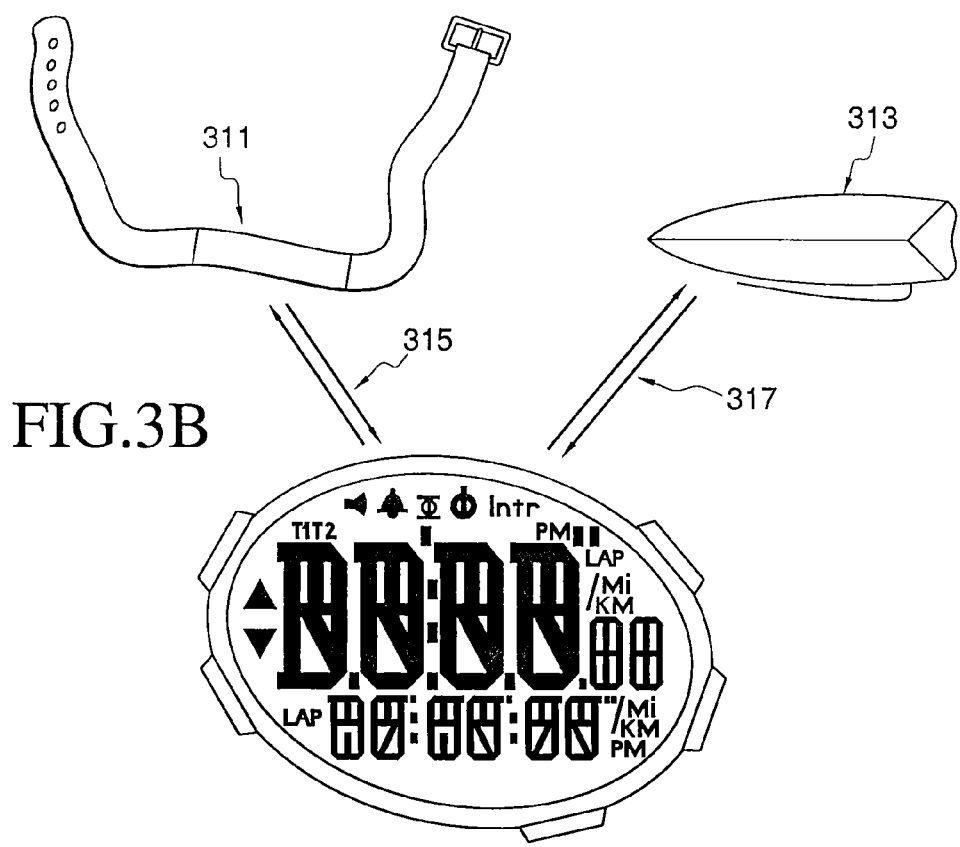

While the above-described embodiment of the invention employs sensors 303 and 305 that only transmit data messages to the watch 301, other embodiments of the invention may use a watch or other type of portable electronic console that works with sensors capable of both receiving and transmitting data messages. For example, as illustrated in FIG. 3B, the watch 301 communicates with sensors 311 and 313 using two-way transmissions 315 and 317, respectively. As with the previous example, the sensor 311 may be a heart rate monitor, while the sensor 313 may be a speed/distance monitor. When the watch 301 is activated, the computing device 103 begins reviewing data messages received by the sensor device interface 115 for approximately one second. In this way, the watch 301 determines what data messages are being sent, and thus what time channels are available for communication with the sensors 311 and 313.

If no other electronic devices are transmitting data messages during this period, then the computing device 103 will itself began transmitting messages to the sensors 311 and 313 through the sensor device 115. The sensors 311 and 313 will then transmit an acknowledgement message to the watch 301, allowing the watch 301 to designate a time channel for communicating with each of those sensors 311 and 313. If, on the other hand, an electronic device is transmitting messages during this period, then the watch 301 will transmit a message to that electronic device signaling that it should begin transmitting messages to another device. The watch 301 will then begin transmitting to the electronic device on another time channel, and wait for the acknowledgement from the electronic device. As with previous embodiment, the watch 301 and the sensors 311 and 313 must complete the training process described above in order to properly communicate.

In the above-described embodiments, the watch 301 recognizes data messages from an appropriate sensor 303, 305, 311 or 313 by decoding the data messages with identification information for that sensor. As will be appreciated by those of ordinary skill in the art, however, other techniques may be employed by the watch 301 to distinguish data messages originating from one sensor from the data messages originating from another sensor. For example, the watch 301 can be configured to recognize only data messages that have been transmitted at specific times (that is, data messages that are being transmitted at a particular frequency). Still further, the watch 301 can be configured to recognize only those data messages that are being transmitted on a carrier wave with a particular frequency. Of course, still other techniques for distinguishing the source of data messages may be employed.

Thus, a watch or other type of portable electronic console according to the invention allows the user to employ the watch or console with multiple remote sensors or other electronic devices. Moreover, by introducing a new electronic device through the training process, a user may add new electronic devices for use with the watch or portable electronic console over time.

Multiple-Tiered Modes

Figure 4:
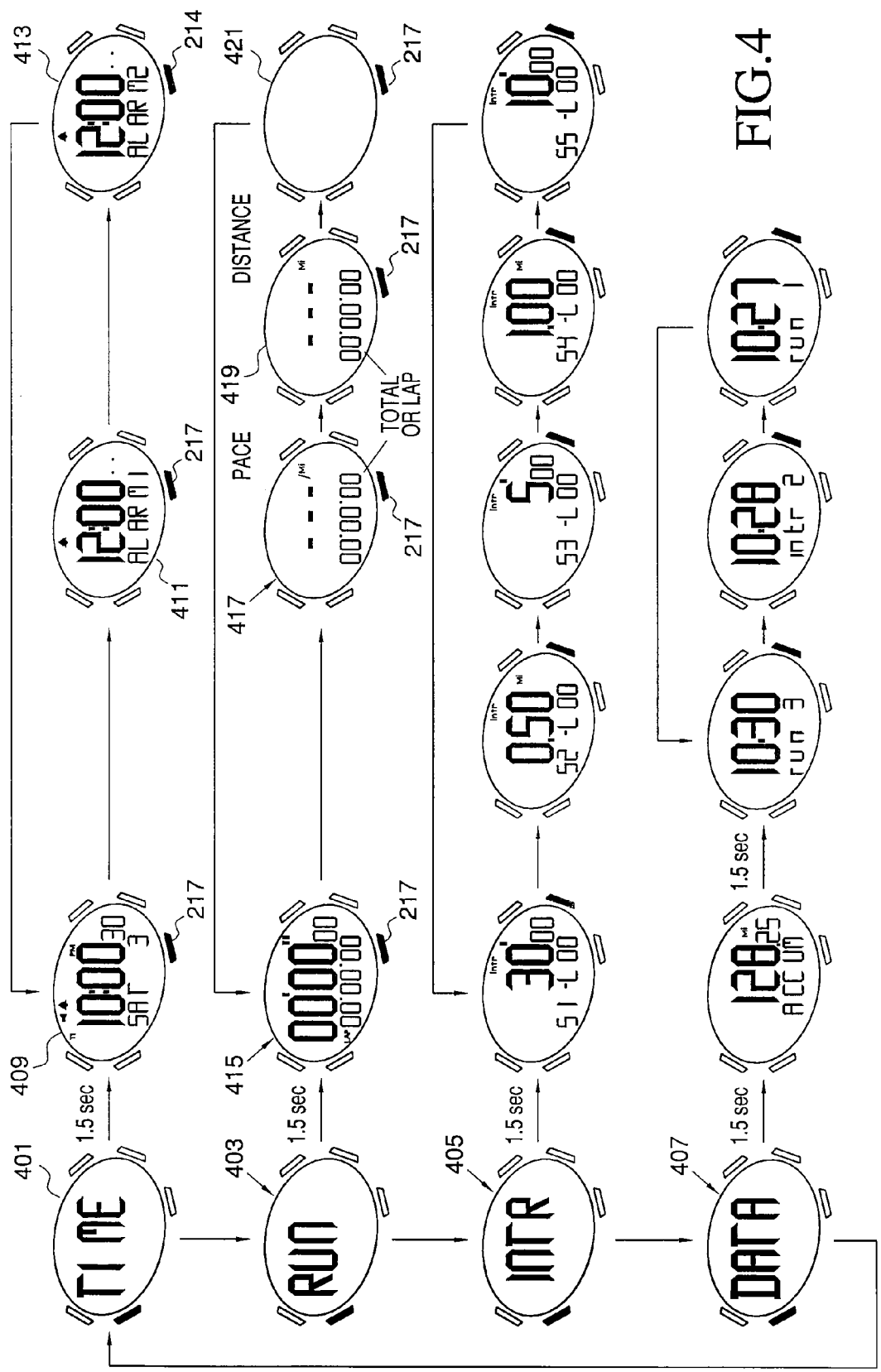
FIG. 4 illustrates of plurality of views generated by the user interface illustrated in FIG. 2.

As previously noted, a watch according to various embodiments of the invention, such as the watch 201 shown in FIG. 2, has two different tiers of operation. The first tier of operation includes operational modes relating to general operations of the watch 201. Each first-tier operational mode then includes one or more second tier operational submodes, each of which relates to more specific functions of the watch 201. For example, as shown in FIG. 4, a watch 201 according to one embodiment of the invention includes four first-tier operational modes, entitled "time," "run," "interval," and "data." As the user switches the watch 201 to each of these first-tier operational modes, the watch 201 displays the corresponding name of that mode. Thus, when the watch 201 is switched to the "time" mode, the watch displays the name of that mode as shown in view 401. The displayed name for the "run" mode is shown in view 403, the "interval" mode is shown in the view 405, and the "data" mode is shown in view 407, respectively. As seen in this figure, a user may scroll through each of the first-tier modes by repeatedly pressing the mode button 211. As also seen in this figure, each first-tier mode includes one or more second-tiered operational submodes.

For example, the first-tier time mode includes the second-tier operational submodes "chronometer," "alarm one," and "alarm two." Thus, after the user has changed the watch 201 to the time mode for 1.5 seconds, the watch 201 shifts into the chronometer submode and displays the current time as shown in view 409. If the user then the depresses the view button 217, the watch 201 shifts into the first alarm submode, and displays the time at which a first alarm is set, as shown in view 411. When the user then presses the button 217 a second time, the watch 201 shifts into the second alarm submode. As seen in the view 413, in the second alarm submode the watch 201 displays the time for which a second alarm is set. If the user then subsequently presses the view button 217 a third time, the watch 201 shifts back into the chronometer submode, and again displays the current time.

Similarly, the first-tier run mode provides access to several second-tier submodes. As seen in FIG. 2, after the user has changed the watch 201 to the run mode for 1.5 seconds, the watch 201 shifts into a chronographic submode, as seen in view 415. In this submode, the primary display field 205 of the watch 201 displays the start values of a chronographic counter. If the user then activates the view button 217, the watch 201 shifts into a pace submode. The primary display field 205 then displays a pace at which the user is traveling, as shown in the view 417. As will be known to those of ordinary skill in the art, this information may be calculated based on, for example, a distance measured by a speed/distance sensor wirelessly communicating with the watch 201. If the user shifts the submode of the watch 201 again by pressing the view button 217, the watch 201 changes into a distance submode, as shown in the view 419. As with the pace submode, in the distance submode the watch 201 obtains distance information from a connected speed/distance monitor.

With the illustrated embodiment, the watch 201 is connected to only a single speed/distance monitor. If, however, the watch 201 were connected to another type of electronic device (as described in detail above) relating to the first-tier run operational mode, then the first-tier run operational mode might include another second-tier operational submode for displaying information provided by that electronic device. For example, if the watch 201 were receiving position information from a global positioning satellite device, then the first-tier run operational mode might include a second-tier operational submode for displaying the position information provided by the global positioning satellite device. The possibility of the use of such an additional second-tier operational mode is graphically illustrated by a blank display shown in the view 421. Of course, if the watch 201 does not include another second-tier operational mode within the run operational mode, then view 421 would be omitted. If the user again depresses the view button 217, the operation of the watch 201 returns to the chronographic mode shown in view 415.

Thus, the invention conveniently allows the user to work with those second-tier submodes of operation immediately relevant to the user, having to scroll through each of the first-tier modes and the other second-tier submodes associated with those first-tier modes. Thus, if a user is running, the user can change the watch 201 to the first-tier run mode, and then shift between all of the second-tier submodes associated with the first-tier run mode, without having to scroll through the time, interval, or data modes. Similarly, if the user is simply using the watch 201 as a conventional watch, the user can shift the operation of the watch 201 to the first-tier time mode, and subsequently view the current time, change the current time, and set one or more different alarms without having to scroll through the run, interval, or data modes.

Configurable Display

Figure 5A:
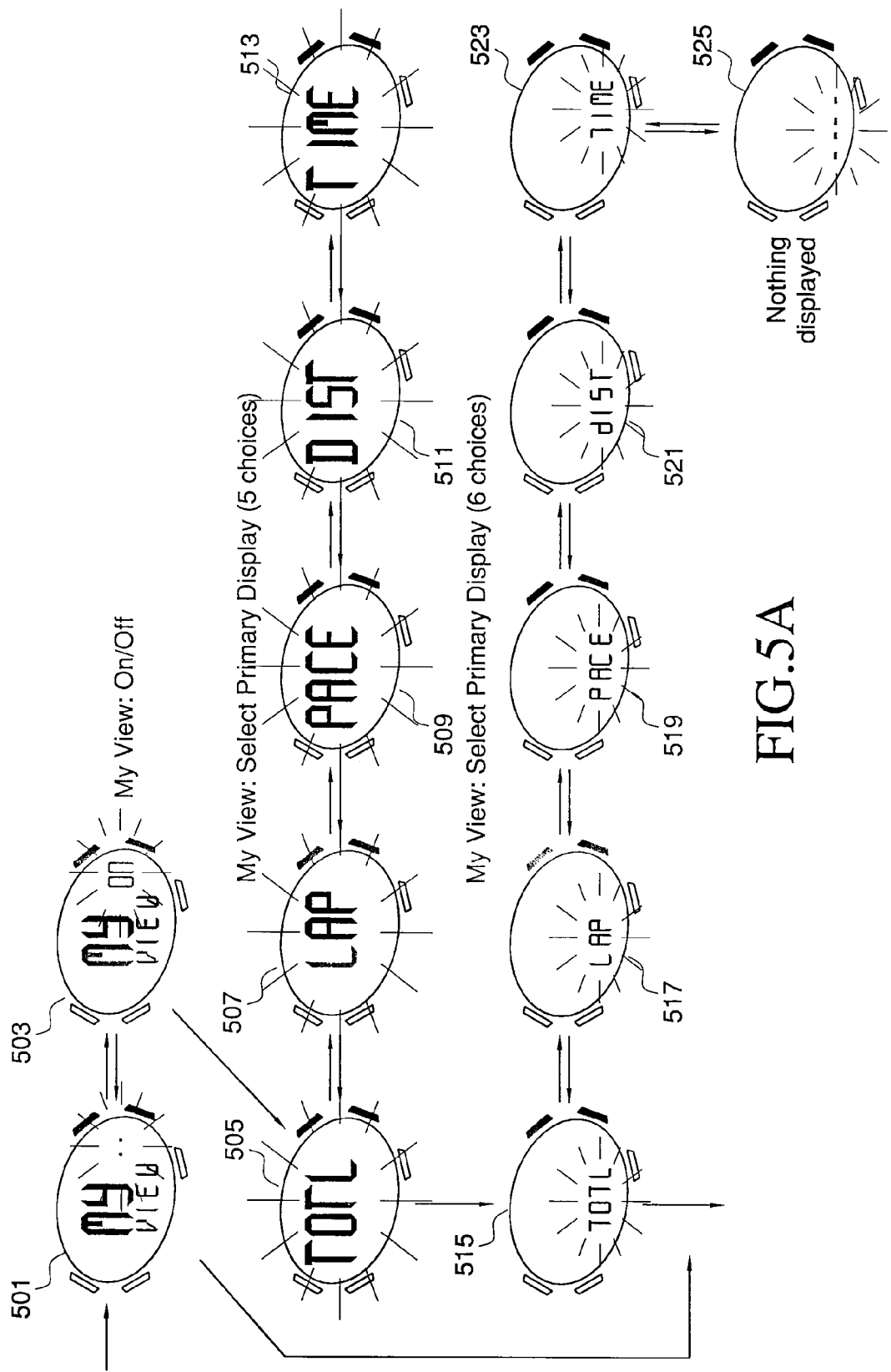

In addition to allowing the user to avoid scrolling through large numbers of different operational submodes, a portable electronic console according to various embodiments of the invention also conveniently allows the user to designate how the information measured by the console in one or more of different modes or submodes will be displayed. For example, the watch 201 illustrated in FIG. 2 may be configured to allow a user to designate what type of information will be displayed in the primary display field 205 and the secondary display field 207, respectively. Referring now to FIG. 5A, when the user has switched the watch 201 to the run mode, the user may designate a number of different settings for use in measuring and displaying parameters associated with the user's athletic activity. These settings include, for example, upper and lower limits on a desired pace for the user, activation or deactivation of an alarm when the user exceeds or falls below these pace limits, and the units in which the pace and distance will be measured.

Another of these settings is the configuration of the display 201. More particularly, during the process of choosing the settings for the run mode, the user will eventually scroll through different views to the access view 501. This access view 501 provides an interface that allows the user to designate which values will be displayed in both the primary display field 205 and the secondary display field 207, respectively, while the chronograph is active (that is, while the chronograph function is measuring a total elapsed time). If the user wishes to personally configure the types of information shown in the display 201, then the user begins the configuration process by activating the start button 213. In response, the watch 201 displays the word "on" to indicate that the user can now designate the type of information to be displayed in the primary display field 205 and the secondary display field 207, as shown in the view 503.

To employ this feature, the user first activates the mode button 211. The primary display field 205 then displays the letters "TOTL" as shown in the view 505, to indicate that the primary display field 205 is now configured to display the total value of a time period measured by the watch 201. To change this default value, the user activates the start button 213 again. In response, the primary display field 205 will be configured to display lap times measured by the watch 201 while the chronographic function is active. This selection for the display 201 is indicated by the immediate display of the letters "LAP" in the primary display field 205, as shown in the view 507.

If the user activates the start button 213 one more time, then the primary display field 205 will display the user's pace while the chronographic function is active, as indicated by the immediate display of the letters "PACE" as shown in the view 509. If the user activates the start button 213 yet again, then the primary display field 205 will display the total distance traveled by the user while the chronographic function is active, as reflected by the immediate display of the letters "DIST" in the view 511. Lastly, if the user activates the start button 213 once again, then the primary display field 205 will display the current time. This selection is indicated by the immediate display of the letters "TIME" in the view 513. It should be noted that, rather than having to scroll through every display configuration to reach a desired display configuration, a user can return to the display configuration immediately preceding the current display configuration simply by activating the stop button 215 instead of the start button 213.

To change the type of information displayed in the secondary display field 207 while the chronograph is active, the user depresses the mode button 211 again. In response, the secondary display field 207 displays the letters "TOTL," as shown in the view 515, indicating that the secondary display field 207 will display the total time value measured by the chronographic function while the chronographic function is active. As will be appreciated by those of ordinary skill in the art, this is the default setting for the secondary display field 207. To have the secondary display field 207 instead display individual lap times measured by the chronographic function while the chronographic function is active, the user activates the start button 213. In response, the secondary display field 207 immediately displays the letters "LAP" as shown in view 507 of FIG. 5A. This indicates that the secondary display field 207 is configured to display individual lap times while the chronographic function is active.

Similarly, if the user would prefer for the secondary display field 207 to display the user's pace while the chronographic function is active, the user may activate the start button 213 again. As shown in view 509 of FIG. 5A, the secondary display field 207 immediately displays the letters "PACE" to indicate that the secondary display fields 207 will display the user's current pace while the chronographic function is active. If the user activates the start button 213 yet again, then the secondary display field 207 will display the total distance traveled by the user while the chronographic function is active. To reflect this setting, the secondary display field 207 will immediately display the letters "dIST," as shown in the view 521.

If the user activates the start button 213 yet again, then the secondary display field 207 will display the current time while the chronographic function is active. To reflect this setting, the secondary display field 207 will immediately display the letters "TIME" as shown in view 523. Lastly, the user may choose to have no information displayed in the secondary display field 207 while the chronographic function is active. To select this choice, the user activates the start button 213 one more time. In response, the secondary display field 207 is cleared as shown in view 525, and remains clear while the chronographic function is active. Again, as with the primary display field 205, rather than scroll forward through each display configuration, a user can select the display configuration immediately preceding the current display configuration simply by activating the stop button 215.

Thus, a user may personally configure both the type and arrangement of information displayed by the display 117. It should be noted, however, that the configuration of the display is not limited to only information displayed while a chronographic function is active. Other embodiments of the invention may allow a user to configure the information displayed by the display 117 at a variety of different times and according to a variety of different formats. For example, some embodiments of the invention may allow a user to select a display configuration for use when the watch 201 is in the time operational mode.

These embodiments may allow the user to select, for example, a display configuration that displays the current time for a first time zone in the primary display field 205 and displays the current time for a second time zone in the secondary display field 207, as shown in view 527 of FIG. 5B. These embodiments may also allow the user to select a display configuration that displays the current time for the second time zone in the primary display field 205 and the current time for the first time zone in the secondary display field 207, as shown in view 529, a display configuration that displays the current 24-hour time for the first time zone in the primary display field 205 and the current 12-hour time for the first time zone in the secondary display field 207, as shown in view 531, and a display configuration that displays the value of, for example, a counter or timer in the primary display field 205 and the current time for the first time zone in the secondary display field 207.

Of course, it should be appreciated that a variety of other display configurations may be employed by various embodiments of the invention, and some embodiments of the invention may have three or more display fields in the display 117. Moreover, the use of a configurable display is not limited to when the watch 201 has an active chronographic function or is in the time operational mode as described above. Instead, various embodiments of the invention may allow a user to configure the type and arrangement of information displayed by the display 117 for any condition of the watch or portable electronic console. Still other embodiments of the invention may allow a user to additionally configure the output device through which desired information is provided to the user. For example, some embodiments of the invention may allow the user to select from among different output configurations that may include, for example, an output configuration where a current time in a first time zone is periodically audibly played for the user through a speaker 119, and a current time for a second time zone is displayed by the display 117, another output configuration where a current time in a first time zone is periodically audibly played for the user through a speaker 119 and the current value of a counter or timer is displayed on the display 117, and still another output configuration where both the current time in the first time zone and the current value of a counter or timer are both periodically audibly played for the user through a speaker 119.

Power Save Function

Still another setting that a user may designate for various embodiments of the invention are the parameters of a power save function. For example, with some embodiments of the watch 201 illustrated in FIG. 2, a user can scroll through various setting interfaces until the user obtains the setting interface shown in view 601 of FIGS. 6A and 6B.

With some embodiments of the invention, the power save function allows the user to designate a time period of inactivity after which the watch 201 shuts down one or more functions to save power. For example, as shown in view 603 of FIG. 6A, the watch 201 may initially display an initial default inactivity period of 5 hours. A user can then increase this value in one hour increments by activating the start button 213, as shown in view 605, or decrease this value in one hour decrements by activating the stop button 215 as shown in view 607. Of course, it should be appreciated that these initial default, increment and decrement values are merely exemplary, and that other embodiments of the invention may employ different initial default, increment and decrement values. Further, various embodiments of the invention may use different input techniques to allow a user to set the inactivity period.

It should also be noted that, according to the invention, the period of inactivity can be determined using a variety of criteria. With some embodiments of the invention, for example, the watch 201 may include an accelerometer for detecting motion of the watch 201. If the accelerometer does not detect motion of the watch for the designated inactivity period, then the watch 201 may enter a power save state. During this state, the watch 201 may, for example, discontinue powering the display 117, the speakers 119, and additional or alternate functions or components. When the accelerometer subsequently detects motion of the watch 201, the watch 201 will leave the power save state and restore power to its shut-down functions and components.

With still other embodiments of the invention, the period of inactivity may be determined based upon inputs to the watch 201. For example, the watch 201 may enter the power save state if a user does not activate one of the command buttons 209-217 for the designated inactivity period. Thus, if the user does not activate one of the command buttons 209-217 for the designated period of time, then the watch will enter the power save state. It should be noted, however, that some embodiments of the invention may take into account input from one or more remote electronic devices when determining if the inactivity period has been exceeded.

With still other embodiments of the invention, the user may designate a specific time at which the watch will both enter and leave the power save state. Thus, after the user has turned the power save setting "on," the display 117 may display a default start time for the watch to enter the power save state as shown in view 609 of FIG. 6B. The user can then adjust the power save start time using one or more of the command buttons 209-217. Once the user has selected the desired start time for the power save state, the display 117 displays a default end time for exiting the power save state, as shown in view 611. Again, the user may change the default end time using the command buttons 209-217. Once the start and end times for the power save state have been selected, the watch 201 will automatically enter and exit the power save state at those times, respectively.

Speed/Distance Monitor Calibration Settings

In addition to allowing a user to designate settings for the watch or portable electronic console itself, the watch or portable electronic console according to some embodiments of the invention may allow a user to designate settings for a remote electronic device communicating with the watch or portable electronic console. As described in detail above, various embodiments of the invention provide for two-way communication with remote electronic devices such as a digital audio player and sensors that measure an athletic performance parameter. Thus, the watch or portable electronic console may send instructions or data to an associated remote electronic device.

For example, referring back to FIG. 3B, the watch 301 can be used to send calibration information to the speed/distance monitor 313. As will be appreciated by those of ordinary skill in the art, the speed/distance monitor 313 illustrated in this figure contains an accelerometer that detects each step of a user's foot. From this, the speed/distance monitor 313 can estimate the distance that a user has traveled. In order to improve this estimate, however, the user can calibrate the speed/distance monitor 313 to multiply its estimate by an offset value. Initially, the default value of this offset value is "1.000."

Figure 7:
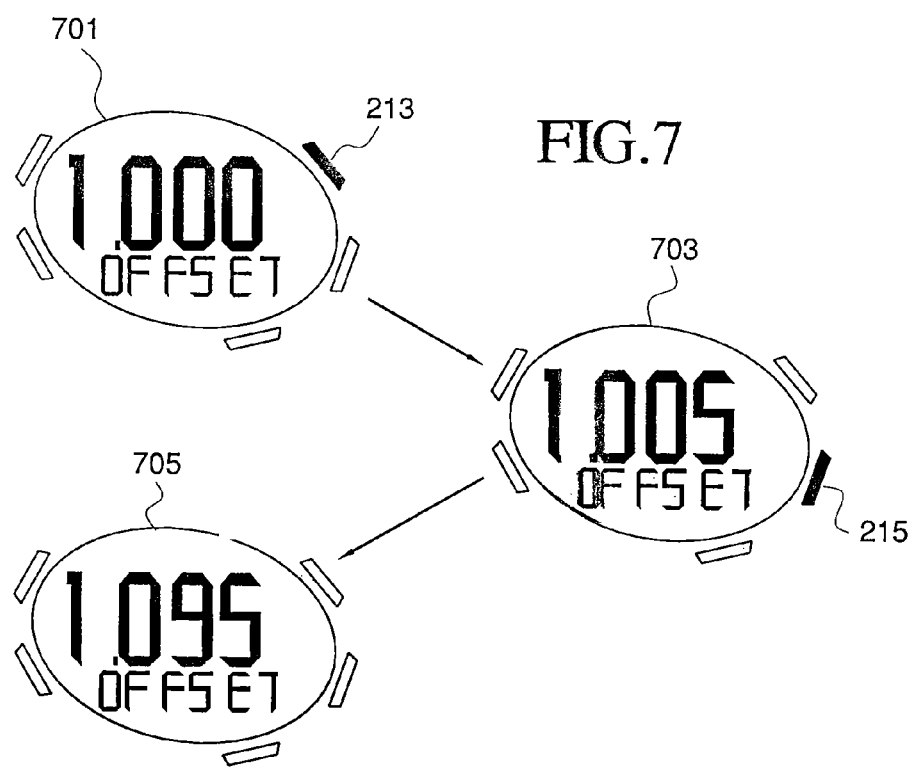
FIG. 7 illustrates interface views that may be employed by various embodiments of the invention to adjust a speed/distance monitor offset.

In some circumstances, however, the user may desire to change this offset value. For example, if the electronic circuitry in the speed/distance monitor 313 is exposed to heat, then the measurements of its circuitry may change. Alternately, a different user may be employing the speed/distance monitor 313 than the user for which the monitor 313 was originally calibrated. In these situations, the user may wish to change the offset value. As shown in FIG. 7, the user may view the current setting using the display 117, as shown in view 701. Using the button 213, the user can then increase the offset in increments of, for example, 0.005, as shown in view 703. Alternately, by depressing the button 215, the user can decrease the offset in increments of 0.005, as shown in view 705. Once the new offset has been selected, the watch 301 will then transmit the new offset to the speed/distance monitor 313. In this way, the user can employ the watch 301 to control the operation of the monitor 313.

Heart Rate Zones Calculation

In addition to settings that may be designated entirely by a user, various embodiments of the invention may assist a user in determining various settings. For example, with some embodiments of the invention, the watch 201 may automatically calculate heart rate zones for a user. As known to those of ordinary skill in the art, an athlete's energy consumption corresponds to his or her heart rate. At heart rates that are only slightly elevated from normal, an athlete will produce energy through aerobic chemical reactions. At higher heart rates, however, an athlete will produce energy through anaerobic chemical reactions. Thus, an athlete can obtain different performance gains by maintaining his or her heart rate within a target range or "zone." For example, an athlete may burn fat most efficiently by maintaining his or her heart rate within the zone that is 40% to 60% of the athlete's maximum heart rate. On the other hand, an athlete may improve his or her maximum possible rate of oxygen consumption by maintaining his or her heart rate within the zone that is 60% to 80% of the athlete's maximum heart rate.

Accordingly, in addition to simply measuring a user's heart rate, various heart rate monitors will also allow a user to designate one or more various heart rate zones, and alert an athlete when his or her measured heart rate goes above or falls below a selected heart rate zone. With these heart rate monitors, however, an athlete must calculate the parameters of these zones himself or herself. This typically requires that the athlete employ a mathematical formula incorporating the athlete's sitting heart rate, the athlete's age, and a general estimate of the athlete's fitness condition. Thus, these formulas are typically difficult for an athlete to calculate. Further, when a user attempts to "shoot" for a number that they have seen on a heart rate chart or have calculated using a heart rate equation, the heart rate values reached using these techniques may be appropriate for a few individuals, by they often are inaccurate for many users because they cannot take into account an individual's particular exercise ability.

Figure 8:
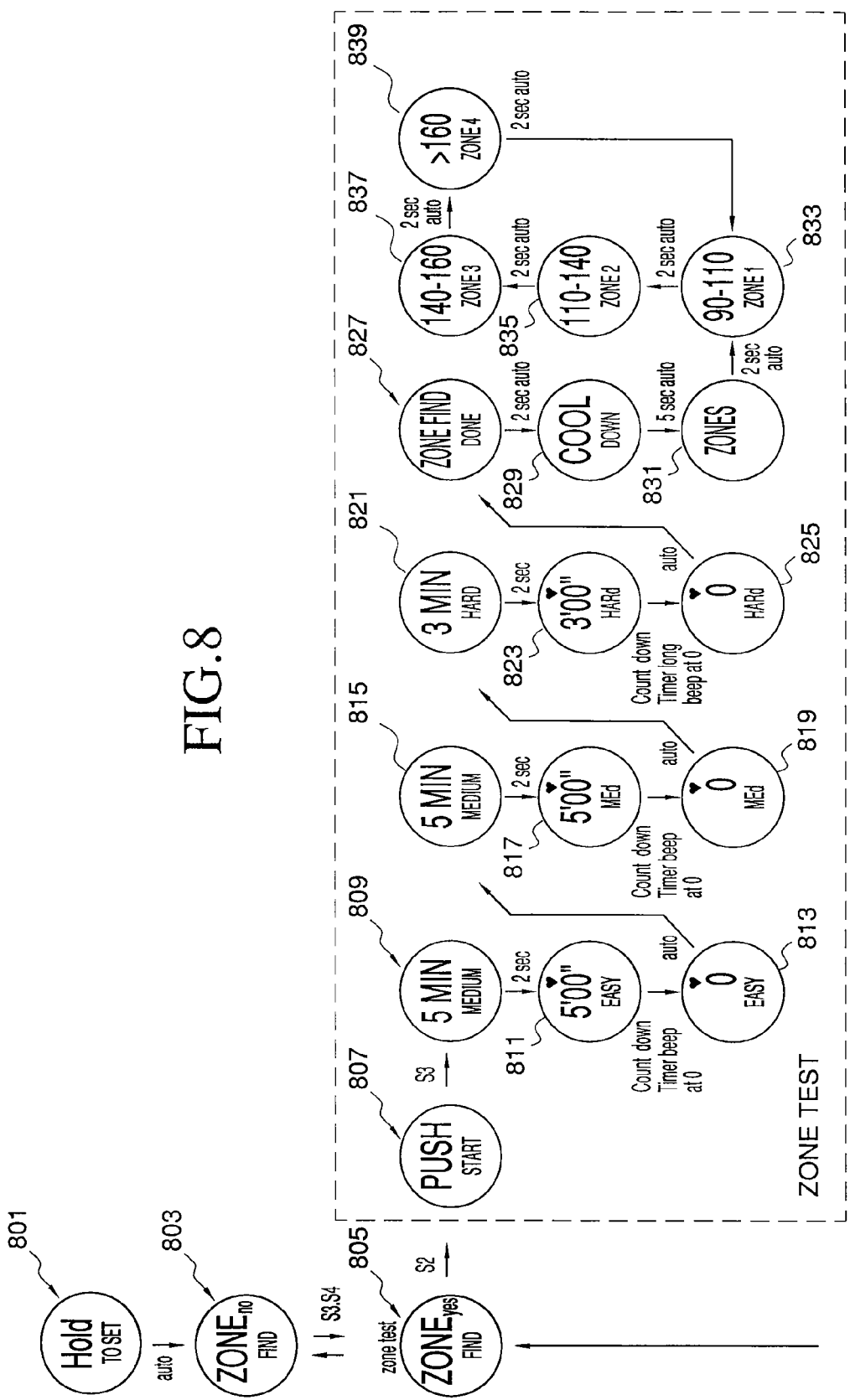
FIG. 8 illustrates interface views that may be employed by various embodiments of the invention to automatically calculate heart rate zones.

To simplify the process of determining heart rate zones, various embodiments of the invention advantageously calculate heart rate zones for an individual athlete automatically. More particularly, various embodiments of the invention allow a user to calculate an individualized heart rate by associating the heart rate with how a user is physically feeling when determining the heart rate. This allows a user to determine the appropriate heart rate to exercise more efficiently and to avoid over-training. With some embodiments of the invention the user can initiate the automatic heart rate zone mode by depressing and holding the set button 209. As shown in FIG. 8, the watch 201 may move from displaying the words "HOLD TO SET," as shown in view 801, to display the words "ZONE FIND" as shown in view 803, to indicate that the user has initiated the heart rate zone calculation mode. The watch also may also display the word "NO," indicating that the watch 201 has not yet been instructed to begin calculating the heart rate zones. To have the watch 201 begin calculating the heart rate zones, the user can depress either the start button 213 or the stop button 215, which changes the displayed word "NO" to "YES," as shown in view 805. The user then depresses the mode button 211, to confirm the initiation of the heart rate zone calculation process. In response, the watch 201 displays the words "PUSH START" as shown in view 807, to indicate to the user that it is ready to begin in the zone calculation process.

When the user is ready to begin exercising, he or she depresses the start button 213. The watch 201 then briefly displays the words "5 MIN EASY," as shown in view 809, instructing the user to begin exercising at an easy level for five minutes. Next, after approximately two seconds the watch 201 begins counting down the amount of time remaining during the five minute period, starting with 5'00" and ending with 0, as shown in views 811 and 813, respectively. It also displays the word "EASY" during this time period, to indicate to the user that he or she should be exercising at an easy level. As will be appreciated by those of ordinary skill in the art, an easy level of exercise is one that only slightly elevates the user's heart rate. This level of exercise should not feel challenging, but should instead feel as if the user is performing a warm-up routine, so that the user feels at ease. The user should be able to maintain this workout intensity for approximately 30 minutes to one hour with his or her breathing only slightly greater than when the user began exercising.

During that time period, a heart rate monitor (such as the heart rate monitor 303 or 311) provides the watch 201 with the user's heart rate, and the watch 201 calculates a representative heart rate for an easy level of exercise. As will be appreciated by those of ordinary skill in the art, a representative heart rate may be calculated using a variety of techniques. For example, with the illustrated embodiment, the watch 201 obtains an average heart rate for the user from the time period beginning one minute after the user has started the easy exercise period to 1.5 minutes into the easy exercise period. This representative heart rate is then designated as the lower limit of the first heart rate zone, sometimes referred to hereafter as the Z1 the lower limit value.

Immediately after the five minute easy exercise period expires, the watch 201 briefly displays the words "5 MIN MEDIUM" as shown in view 815, to indicate to the user that a period of medium level exercise is about to begin. Again, after approximately two seconds the watch 201 begins counting down the amount of time remaining during the five minute period, starting with 5'00" and ending with 0, as shown in views 817 and 819, respectively. It also displays the word "MED" during this time period, to indicate to the user that he or she should be exercising at a medium level of exertion. As will be appreciated by those of ordinary skill in the art, a medium level of exertion is one that is more challenging than a warm-up, but not uncomfortable. The user should be able to maintain this workout intensity for at least 20-40 minutes without difficulty. Also, the user's breathing should be heavy, with the user having no difficulty obtaining air.

As the user is performing the medium level of exercise, the watch 201 obtains a heart rate representative of this level of exertion. Again, this representative heart rate may be calculated in a variety of different ways. With the illustrated embodiment of the invention, the watch 201 obtains the user's average heart rate from the beginning of the medium exercise period to one minute into the medium exercise period. This average heart rate value is then designated the upper limit of the first heart rate zone (sometimes referred to hereafter as the Z1 upper limit value), and the lower limit of the second heart rate zone, sometimes referred to hereafter as the Z2 lower limit value.

Immediately after the medium level exercise period is concluded, the watch 201 begins hard level period of exercise. More particularly, as shown in the view 821, the watch 201 briefly displays the words "3 MIN HARD", to indicate to the user that a period of hard level exercise is about to begin. Again, after approximately two seconds the watch 201 begins counting down the amount of time remaining during the three minute period, starting with 3'00" and ending with 0, as shown in views 823 and 825, respectively. It also displays the word "HARd" during this time period, to indicate to the user that he or she should be exercising at a hard or difficult level of exertion. As will be appreciated by those of ordinary skill in the art, a hard level of exertion should significantly challenge the user. That is, this level of exercise should be achievable, but not comfortable, and should feel like the user is exercising at a competitive pace. The user's breathing should be heavy, and the user should not be getting sufficient air to continue this level of exercise for a long period time. The user should be able to maintain this intensity of exercise for only approximately 3 to 5 minutes.

Because this level of exercise significantly strains the user, the watch 201 will obtain two representative heart rate values during the hard exercise period. One value corresponds to the upper limit of the heart rate zone associated with a medium level workout, while the second value corresponds to the upper limit of the heart rate zone associated with a hard level work out. Again, the representative heart rate values can be calculated using any variety of desired techniques. For example, with some embodiments of the invention, the watch 201 will calculate the first value (sometimes referred to hereafter as the Z2 upper limit value or the Z3 lower limit value) by taking the user's average heart rate from the beginning of the hard exercise period to 30 seconds into the hard exercise period. These embodiments will calculate the second value (sometimes referred to hereafter as the Z3 upper limit value or the Z4 lower limit value) by averaging the user's heart rate for the remaining time in the hard exercise period (that is, from 30 seconds into the hard exercise period until the end of the hard exercise period).

Alternately, other embodiments of the invention may calculate the Z2 upper limit value or the Z3 lower limit value by obtaining the user's average heart rate during the first minute of the hard exercise. These embodiments will then calculate the Z3 upper limit value or the Z4 lower limit value by obtaining the user's average heart rate for the remaining time in the hard exercise period (that is, from one minute into the hard exercise period until the end of the hard exercise period). Still other embodiments of the invention will calculate the Z2 upper limit value or the Z3 lower limit value by obtaining the user's average heart rate for the last 30 seconds of the medium exercised period and the first 30 seconds of the hard exercise period. These embodiments will then calculate the Z3 upper limit value or the Z4 lower limit value by obtaining the user's average heart rate during the last minute of the hard exercise period.

Once the watch 201 has completed calculating the various limits of the heart rate zones, the watch 201 briefly displays the words "ZONE FIND DONE" as shown in view 827, to inform the user that the heart rate zones have been calculated. Then, as shown in view 829, the watch 201 displays the words "COOL DOWN" to instruct the user to begin a cooling down period of exercise, in order to gradually reduce the user's heart rate to a normal value. The watch 201 then displays the word "ZONES" as shown in view 831, to warn the user that it is about to display the upper and lower limit values for each heart rate zone that it has just calculated. Next, as shown in view 833, the watch 201 displays the Z1 lower limit value and the Z1 upper limit value for the first heart rate zone. In the illustrated embodiment, these values are a heart rate of 90 beats per minute and a heart rate of 110 beats per minute, respectively. The watch 201 then displays the Z2 lower limit value and the Z2 upper limit value for the second heart rate zone, as shown in view 835. With the illustrated embodiment, these values are a heart rate of 110 beats per minute and a heart rate of 140 beats per minute, respectively. The watch 201 then displays the Z3 lower limit value and the Z3 upper limit value for the third heart rate zone, as illustrated in view 837. With the illustrated embodiment, these values are a heart rate of 140 beats per minute and 160 beats per minute, respectively. Finally, the watch 201 displays the Z4 lower limit, which in the illustrated embodiment has the value of 160 beats per minute, indicating the lower limit of the fourth heart rate zone.

CONCLUSION

There are any number of alternative combinations for the invention, which incorporate one or more elements from the specification, including the description, claims, and drawings, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations. For instance, in various embodiments, a certain order to the data has been shown. However, any reordering of the data is encompassed by the present invention. Also, where certain units of properties such as size (e.g., in bytes or bits) are used, any other units are also envisioned.

What is claimed is:

1. A method of determining a heart rate zone by a portable electronic device configured for attachment to a user, the method comprising:
   prompting the user, by the portable electronic device, to exercise at a first level of exertion;
   calculating, by the portable electronic device, a first representative heart rate based on a first measurement of the user's heart rate after instructing the user to exercise at the first level of exertion;
   designating the first representative heart rate as a lower limit value for the heart rate zone;
   prompting the user, by the portable electronic device, to exercise at a second level of exertion more strenuous than the first level of exertion;
   calculating, by the portable electronic device, a second representative heart rate based on a second measurement of the user's heart rate after instructing the user to exercise at the second level of exertion; and
   designating the second representative heart rate as an upper limit value for the heart rate zone.

2. The method of determining a heart rate zone recited in claim 1, further comprising:
   designating the second representative heart rate as a lower limit value for a second heart rate zone;
   instructing a user to exercise at a third level of exertion more strenuous than the second level of exertion;
   calculating a third representative heart rate based on a third measurement of the user's heart rate after instructing the user to exercise at the third level of exertion; and
   designating the third representative heart rate as an upper limit value for the second heart rate zone.

3. The method of determining a heart rate zone recited in claim 2, further comprising:
   designating the third representative heart rate as a lower limit value for a third heart rate zone.

4. The method of determining a heart rate zone recited in claim 2, wherein a period of time the user is prompted to exercise at the third level of exertion is shorter than a duration of time the user is instructed to exercise at the second level of exertion.

5. The method of determining a heart rate zone recited in claim 1, wherein the first level of exertion corresponds to aerobic exercise for the user and the second level of exertion corresponds to anaerobic exercise for the user.

6. The method of determining a heart rate zone recited in claim 1, wherein the step of instructing a user to exercise at a first level of exertion is performed for a period of time.

7. The method of determining a heart rate zone recited in claim 6, wherein the first representative heart rate is obtained by calculating an average heart rate of the user for at least a portion of the period of time.

8. The method of determining a heart rate zone recited in claim 1, wherein the step of instructing a user to exercise at a second level of exertion is performed for a period of time.

9. The method of determining a heart rate zone recited in claim 8, wherein the second representative heart rate is obtained by calculating an average heart rate of the user for at least a portion of the period of time.

10. The method of determining a heart rate zone recited in claim 8, wherein the period of time is shorter than a duration of time the user is instructed to exercise at the first level of exertion.

11. The method of determining a heart rate zone recited in claim 1, wherein the portable electronic device is a watch device.

12. The method of determining a heart rate zone recited in claim 11, wherein the watch device communicates at least one of audio and visual instructions.

13. A method of instructing exercise, comprising the steps of:
   determining a heart rate zone having a first representative heart rate and a second representative heart rate, the heart rate zone determined in accordance with claim 1; and
   instructing a user to exercise for a first period of time so that the user's heart rate is between the first representative heart rate and the second representative heart rate.

14. The method of instructing exercise recited in claim 13, further comprising the steps of:
   after the first period of time, instructing the user to exercise for a second period of time so that the user's heart rate exceeds the second representative heart rate.

15. The method of instructing exercise recited in claim 14, wherein a duration of the second period of time differs from a duration of the first period of time.

16. The method of instructing exercise recited in claim 13, wherein the first period of time is a warm-up for the user.

17. A method comprising:
   determining a heart rate zone for a user, comprising the steps of:
      prompting the user, by a portable electronic device configured for attachment to the user, to exercise at a first level of exertion;
      calculating, by the portable electronic device, a first representative heart rate based on a first measurement of the user's heart rate after instructing the user to exercise at the first level of exertion;
      designating the first representative heart rate as a lower limit value for the heart rate zone;
      prompting the user, by the portable electronic device, to exercise at a second level of exertion more strenuous than the first level of exertion;
      calculating, by the portable electronic device, a second representative heart rate based on a second measurement of the user's heart rate after instructing the user to exercise at the second level of exertion; and
      designating the second representative heart rate as an upper limit value for the heart rate zone;
      instructing the user to exercise;
      determining the user's heart rate during the exercise; and
      alerting the user if the user's heart rate is not within the heart rate zone.

18. The method recited in claim 17, wherein the calculating of the first representative heart rate comprises calculating an average heart rate of the user's heart rate for at least a portion of a period of time in response to prompting the user to exercise at the first level of exertion.

19. The method recited in claim 17, wherein the step of instructing the user to exercise includes instructing the user to exercise so that the user's heart rate is between the first representative heart rate and the second representative heart rate.

20. The method recited in claim 17, wherein the portable electronic device is a watch device.

21. The method recited in claim 20, wherein the watch device communicates at least one of audio and visual instructions.

22. A system comprising:
   a heart rate sensor configured for determining a heart rate of a user;
   a computing system configured for attachment to the user, the computing system in electronic communication with the heart rate sensor, the computing system comprising:
      a processor; and
      a memory storing computer executable instructions that, when executed by the processor, cause the computing system to perform operations comprising:
   prompting the user to exercise at a first level of exertion;
   obtaining a first representative heart rate for the user from the heart rate sensor after instructing the user to exercise at the first level of exertion;
   designating the first representative heart rate as a lower limit value for a heart rate zone;
   prompting the user to exercise at a second level of exertion more strenuous than the first level of exertion;
   obtaining a second representative heart rate for the user from the heart rate sensor after instructing the user to exercise at the second level of exertion; and
   designating the second representative heart rate as an upper limit value for the heart rate zone.

23. The system recited in claim 22, further comprising a speed and distance sensor for determining the speed and distance of the user and wherein the speed and distance sensor is in electronic communication with the computing system.

24. The system recited in claim 23, wherein the computing system comprises an output element for outputting the data sensed by the heart rate sensor, the speed and distance sensor, and the prompts to the user to exercise.

25. The system recited in claim 24, wherein the output element provides one or both of audio and visual output.

26. The system recited in claim 22, wherein the computing system is a watch.

27. A system comprising:
   a plurality of sensors including at least one heart rate sensor configured for determining a heart rate of a user;
   a watch configured for attachment to the user, the watch in electronic communication with each of the sensors, wherein the watch comprises:
      a processor; and
      a memory storing computer executable instructions that, when executed by the processor, cause the watch to perform operations comprising:
   prompting the user to exercise at a first level of exertion;
   obtaining a first representative heart rate for the user from the at least one heart rate sensor after instructing the user to exercise at the first level of exertion;
   designating the first representative heart rate as a lower limit value for a heart rate zone;
   prompting the user to exercise at a second level of exertion more strenuous than the first level of exertion;
   obtaining a second representative heart rate for the user from the at least one heart rate sensor after instructing the user to exercise at the second level of exertion; and
   designating the second representative heart rate as an upper limit value for the heart rate zone.

28. The system recited in claim 27, wherein the watch prompts the user to exercise by one or both of audio or visual output.

* * * * *